(12) United States Patent
Conti (10) Patent No.: US 7,018,327 B1
(45) Date of Patent: Mar. 28, 2006

(54) TEST APPARATUS PROVIDING PULSATILE FLOW SERVICE FOR TEST SAMPLES

(76) Inventor: James C. Conti, 105 E. 4th St., Galena, MO (US) 65656

( * ) Notice: Subject to any disclaimer, the term of this patent is extended or adjusted under 35 U.S.C. 154(b) by 371 days.

(21) Appl. No.: 10/649,589

(22) Filed: Aug. 27, 2003

Related U.S. Application Data (60) Provisional application No. 60/406,282, filed on Aug. 27, 2002.

(51) Int. Cl.
*A61N 1/362* (2006.01)

(52) U.S. Cl. .................. 600/16; 434/268; 73/866.4

(58) Field of Classification Search ........... 600/16–18; 434/262–272; 73/866.4; 606/185
See application file for complete search history.

(56) References Cited

U.S. PATENT DOCUMENTS 2,556,043 A * 6/1951 Roucka .................. 434/268
6,843,145 B1 * 1/2005 Jaszczak et al. .......... 73/866.4
2002/0022857 A1 * 2/2002 Goldsteen et al. .......... 606/185

* cited by examiner

*Primary Examiner*—George Manuel
(74) *Attorney, Agent, or Firm*—Jonathan A. Bay (57) ABSTRACT

A test apparatus provides pulsatile flows that replicate the human cardiovascular system for qualifying implantable cardiovascular devices before implantation in a patient. A pump provides flow pulses to a mock left ventricle, a mock aortic valve, and a mock aorta. A loop from the ventricle to the aorta bypasses the mock aortic valve and affords connection of the test device. The mock aorta comprises elastic tube sections serially connected in progressively diminishing diameters, and interconnected by adjustable flow restrictors. Each elastic tube section shows about 7% to 12% inside-diameter expansion for 100 mm mercury step increase. A designer's choice over the elasticity of the tube sections and a user's control over the flow restrictor(s) allows the user to shape various target waveforms in regards of flowrate and pressure against time as well as the peaks and drop-off forms in addition.

21 Claims, 4 Drawing Sheets

TEST APPARATUS PROVIDING PULSATILE FLOW SERVICE FOR TEST SAMPLES

CROSS-REFERENCE TO PROVISIONAL APPLICATION(S)

This application claims the benefit of U.S. Provisional Application No. 60/406,282, filed Aug. 27, 2002, which provisional application is incorporated herein in full by this reference.

This application is concurrently filed with commonly-invented, commonly-owned co-pending U.S. patent application Ser. No. 10/650,088 [not yet known, to be inserted by applicant's attorney], entitled "Lost Candy Method with Cores or Molds, and Composition," and which is based on U.S. Provisional Application No. 60/405,887, filed Aug. 27, 2002, all the foregoing which are incorporated herein in full by this reference.

BACKGROUND AND SUMMARY OF THE INVENTION

The invention relates to test apparatus and, more particularly, to test apparatus providing pulsatile flow service for test samples. Example test samples include without limitation artificial heart devices or—in more particular reference to the non-limiting exemplary test sample chosen for convenience purposes only to explain the details of the invention—left ventricle assist devices (LVAD's) and so on.

A number of additional features and objects will be apparent in connection with the following discussion of preferred embodiments and examples.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the appended claims. In the drawings.

DETAILED DESCRIPTION OF THE PREFERRED EMBODIMENTS

Figure 1:
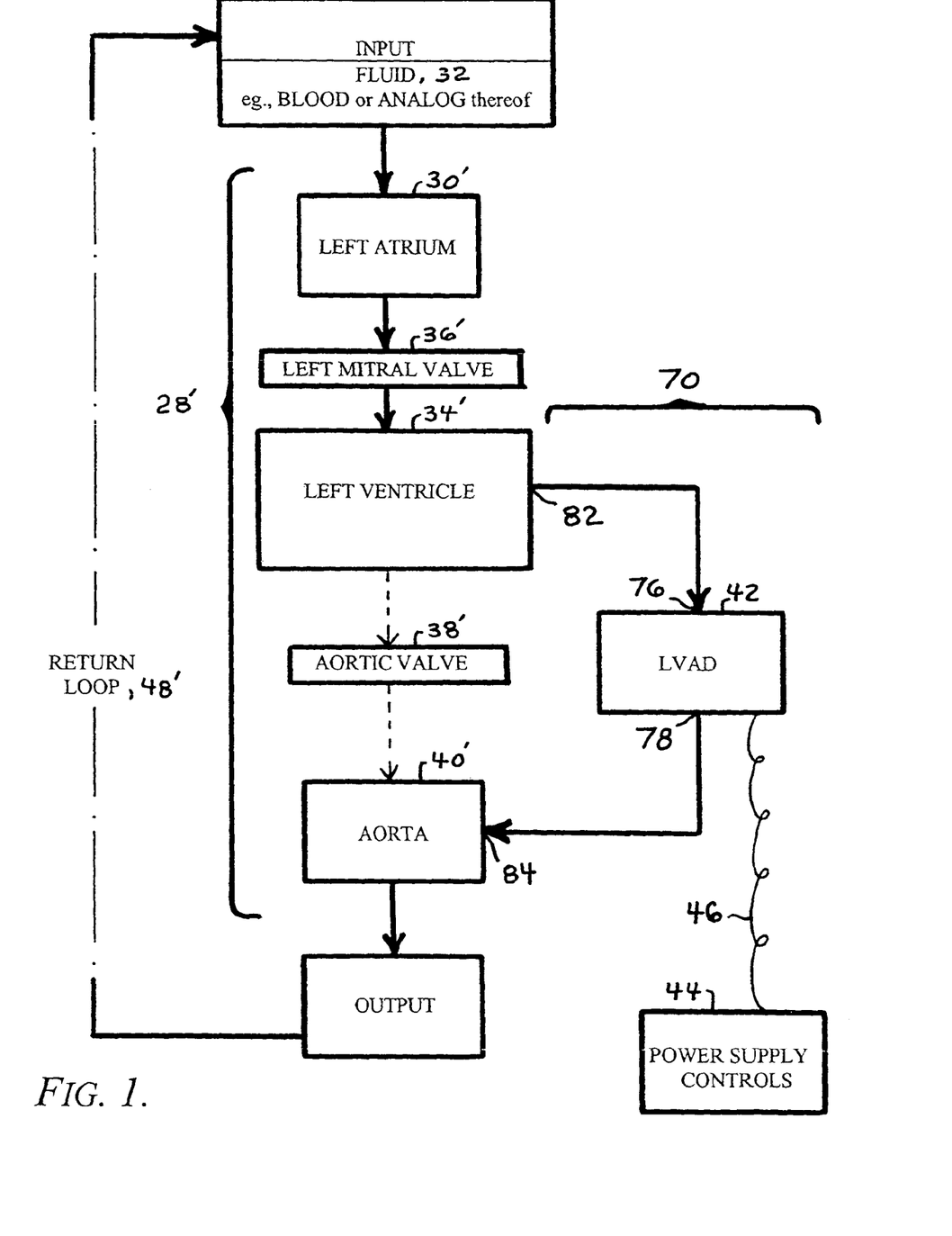
FIG. 1 is a block diagram showing a left ventricle assist device (LVAD) connected in a bypass manner around a (mock) aortic valve between a (mock) left ventricle and (mock) aortic artery, wherein the depicted aortic valve, left ventricle and aortic artery and so on can be alternatively interpreted as block representations of true physiology or else as the mock-up analogs provided by a test apparatus in accordance with the invention, an example embodiment being shown more particularly next.

FIG. 1 is a block diagram that very approximately models in block drawing style aspects of the left side 28' of an, eg., human heart, including as well portions of the aorta 40'. Briefly, the left side 28' is the high-pressure or workhorse side of the human heart. It is supplied oxygen-enriched blood from the lungs and then pumps that supply through the rest of the cardiovascular system, excluding the right side and lungs. Heart treatments and procedures are most often concerned with the left side.

FIG. 1 shows the left atrium 30' receiving an infeed of a circulating fluid 32 (in real life of course, it would be blood). The left ventricle 34' suctions the circulating fluid 32 from the left atrium 30' through the left mitral valve 36'. In a non-assisted heart, the left ventricle 34' outputs the in-drawn blood 32 through the aortic valve 38' and thus to the aorta 40'. One treatment or procedure for diseased or defective hearts involves the positioning of a left ventricle assist device (LVAD) 42 in a loop 70 bypassing the aortic valve 38', thus drawing blood 32 from the left ventricle 34' and outputting the bypass flow directly to the aorta 40'. As an aside, FIG. 1 also shows that a conventional LVAD 42 might require the services of an external power supply and/or controller 44 connected for instance and without limitation by wire conductors 46 as shown.

Figure 2:
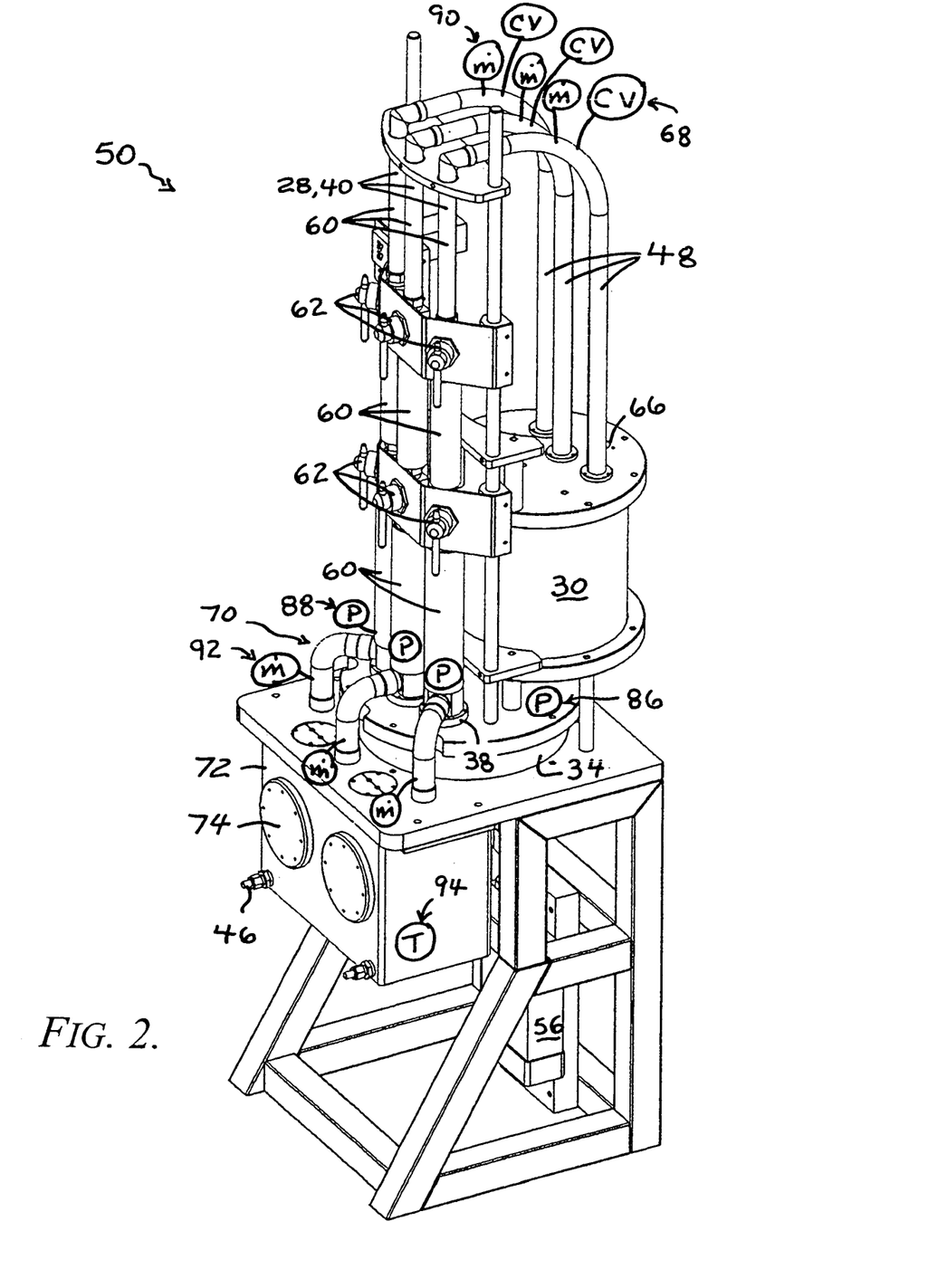
FIG. 2 is a perspective view of a test apparatus in accordance with the invention for providing pulsatile flow service for test samples.
Figure 3:
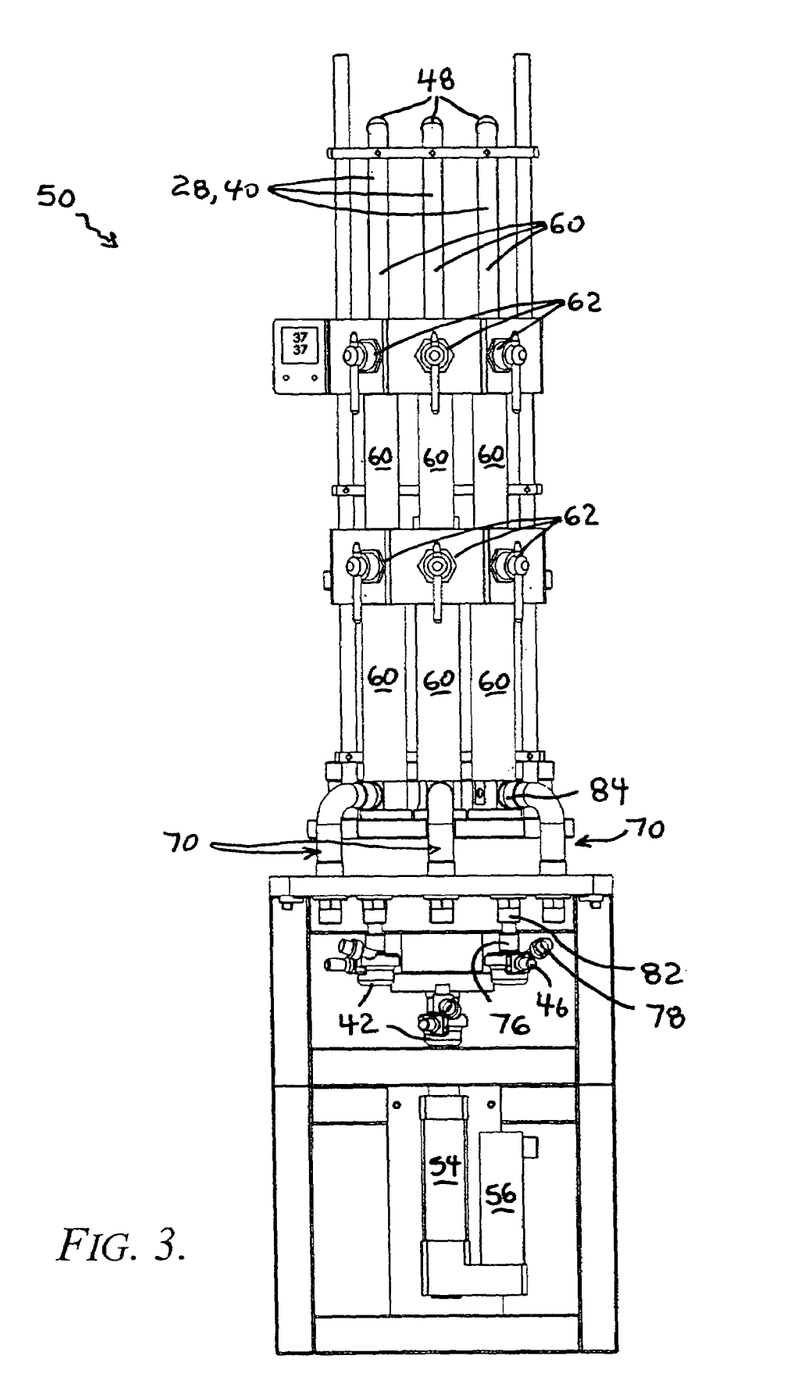
FIG. 3 is a front elevational view thereof, except that a bath tank has been removed to show fixture of test samples to the test apparatus.
Figure 4:
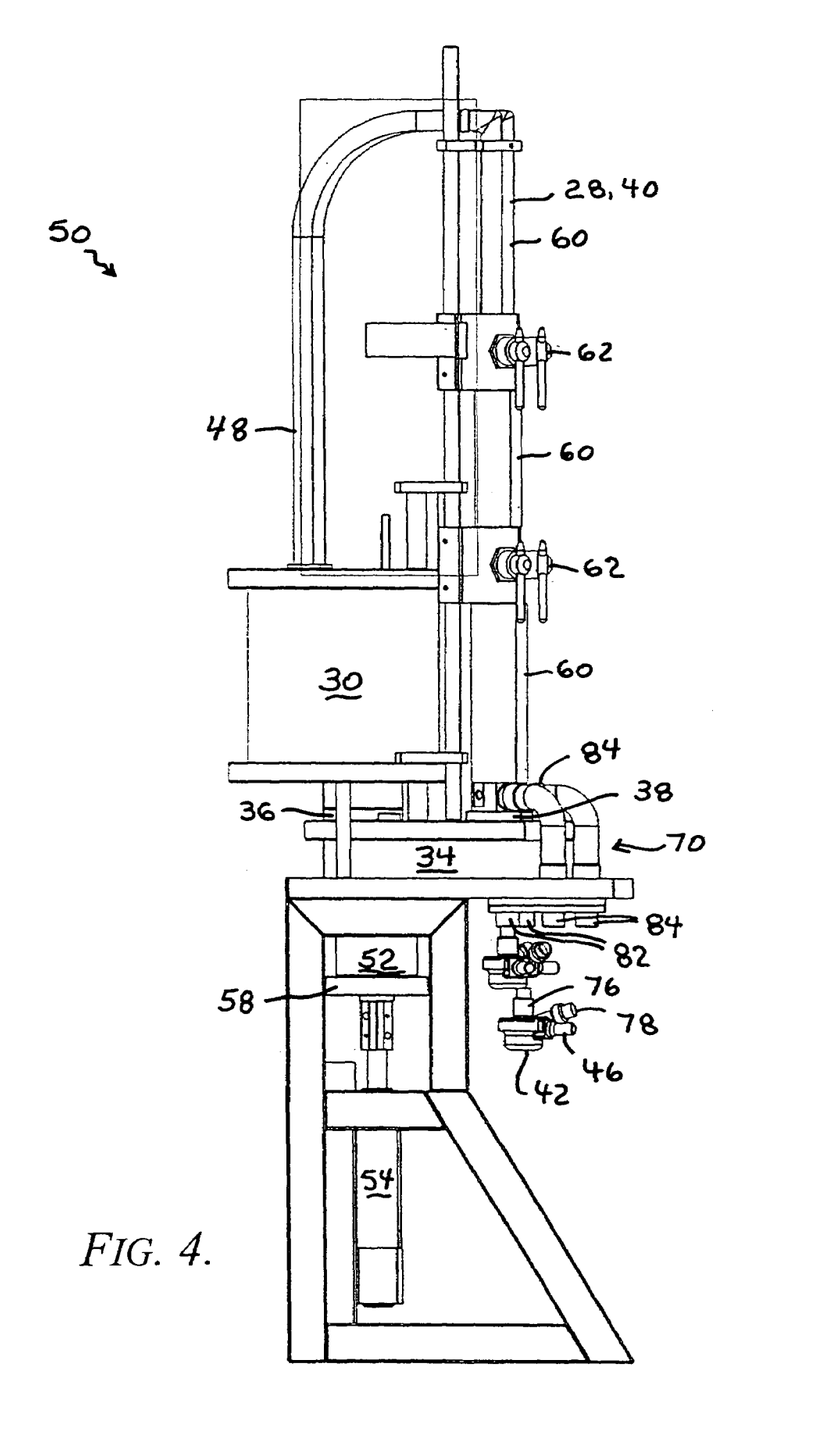
FIG. 4 is a left side elevational view of FIG. 3.

FIGS. 2 through 4 show a test apparatus 50 in accordance with the invention providing pulsatile flow service for test samples (e.g., 42 in FIGS. 3 and 4). As suggested by FIG. 1, one example test sample for the inventive apparatus 50 includes without limitation LVAD's. It is desirable to test LVAD's (or otherwise qualify or certify) their operability and/or reliability to a fairly significant extent before surgically implanting one in a patient.

It is an object of the invention to physically replicate aspects of the human cardiovascular system so that test samples are serviced by flows and conditions that give the test sample a fairly real trial of operating in the environment of the human cardiovascular system.

One way of achieving the foregoing object of the invention includes the test apparatus 50 of FIGS. 2 through 4. In brief overview, the apparatus 50 includes a mock left atrium 30, a mock left mitral valve (not in view in any drawing but its embedded position is indicated by reference numeral 36 in FIG. 4), a mock left ventricle 34, a mock aortic valve (not in view in any drawing but its embedded position is indicated by reference numeral 38 in FIGS. 2 and 4) and a mock aorta 40 connected in a circuit by means of a return loop 48.

It is another object of the invention that from among the mock components which it most sensitively models the characteristics of the real world system 28' (human cardiovascular or whatever it may be), this consists of the mock aorta 40. One way in which the mock aorta 40 is so sensitively modeled is because of its compliant components 60 described more particularly below.

With general reference to FIGS. 2 through 4, the mock left ventricle 34 optionally comprises a cylindrical plenum preferably having a transparent sidewall of glass or plastic set on a test-stand's bench top of stainless steel or the like and capped by a lid also of stainless steel or the like. The pressure pulses are supplied by a piston (not in view in any drawing) that reciprocates in its bore or cylinder 52 shown by FIG. 4. The piston's seal is achieved by a rolling seal (not in view in any drawing) having the configuration of a single pleat of an accordion-style diaphragm. The mechanical drive of the piston (eg., see reference numeral 52 in FIG. 4) is supplied by a ball-screw linear actuator 54 (see FIG. 3 or 4) driven by a servomotor 56 (see FIG. 2 or 3) coupled by a pulley-and-belt drive (not in view in any drawing but see FIG. 3). FIG. 4 shows a combination drip pan and mechanical stop 58 attached on the piston rod to both protect the actuator 54 and servomotor 56 from overhead leaks (if any) as well as to operate as a mechanical limit to prevent over-extension of the piston's seal (eg., inside of the bore or cylinder 52).

For present purposes—excluding one or more bypass loops (eg., plural bypass loops 70 as indicated in FIG. 3) that service test samples 42 such as LVAD's or the like (and more particularly described below)—the output of the mock left ventricle 34 flows through a mock aortic valve 38 that has a flapper design, with butterfly wings that are preferably flexible and produced from a suitable polymer or resinous material. This last-mentioned output flow thus enters the mock aorta 40.

Pause can be taken to consider various features of the inventive test apparatus 50. It incorporates not one but plural aortic valves 38 and aortas 40. For instance the drawings show three such mock aorta structures 40 in parallel. However, the number of three is chosen for convenience of design and is not limiting to the invention as a whole because other numbers can be chosen and configured in accordance with the principles of the invention.

More significantly, the construction of any given aorta 40 is the product of an iterative design effort wherein a prototype version is built and measured for performance, which if not satisfactory a successive prototype is built and measured, and so on until a satisfactory design is converged upon. FIGS. 2 through 4 show one such configuration for how a mock aorta structure 40 might be satisfactorily configured in accordance with the objects of the invention. Each mock aorta structure 40 comprises three sections 60 of elastic tubing inter-coupled by adjustable restrictors 62 such as ball valves or the like. These elastic tubing sections 60 are specially produced articles obtained by dipping cylindrical mandrels in a silicone composition through a repetitive dip-and-cure routine until something approximating a 12-inch (thirty cm) long tube has a given wall thickness by which the elastic tube as a whole has the following physical property(ies), namely:—there is a 7% to 12% expansion of the inside diameter for a 100 mm mercury step increase of inside pressure over the outside pressure, typically atmospheric pressure or close thereto.

The inventor hereof refers to this property as compliance, which allows use of terminology as follows:—a given elastic tube section 60 is designed and built to have between 7% to 12% compliance for each 100 mm mercury of pressure pulse. Depending on the inside diameter and material of the elastic tube 60, the wall thickness varies. As better shown by FIG. 3, the tube sections 60 of each aorta structure 40 decrease in diameter in the progression from lowest, middle and top and as separated by ball valves 62. This progression of progressively constricting inside diameters is another design factor involved in achieving the overall targeted performance of the mock aorta. That is, in each column of tube sections 60 that constitute a single aorta structure 40, the first in the series closest to the mock aortic valve 38 and left ventricle 34 is largest in diameter. The next tube section 60 in the series is progressively smaller in diameter. The succeeding tube section 60 in the series is progressively smaller in diameter still than the preceding tube section 60. Although the aorta structures 40 shown in the drawings are constructed of three tube sections 60 in such a progressive series, the series could be continued indefinitely whereby preferably each succeeding member is of a progressively smaller diameter than the succeeding member until a given useful limit is reached.

For purposes of modeling human cardiovascular characteristics, sufficient results to date are obtained by constructing each aorta structure 40 from a series of three tube sections 60. As previously mentioned, each tube section is a product of a specific process for obtaining the desired compliancy properties. For instance, the largest diameter tube sections 60 are those which in FIGS. 2 through 4 constitute the lowest tier of tube sections 60, or in other words the tube sections 60 which rise up off the mock ventricle 34's lid. These largest diameter tube sections 60 are produced by a process whereby two-inch (five cm) diameter mandrels are dipped in an uncured silicone composition and then cured, and by and through a repetitive dip-and-cure routine something approximating a twelve-inch (thirty cm) long tube is produced with a given wall thickness by which the elastic tube as a whole has the targeted physical property (ies), namely:—a 7% to 12% expansion of the inside diameter for a 100 mm mercury step increase of inside pressure over the outside pressure (typically atmospheric). Again, depending on the material used for producing the elastic tube 60, the wall thickness varies.

Among other things to note about this design include the following. This mock aorta design of elastic or "compliant" components 60 allows better modeling or simulation of the mean characteristics of a healthy human cardiovascular system. These mean characteristics are defined or described by pressure against time profiles, flowrate against time profiles, and to a lesser extent temperature against time profiles. Briefly, a healthy human heart is characteristically a two-psi (100 mm of mercury) pulsing system but instead of the waveform being symmetric, it is instead typically referred to as being pulsatile. More particularly, the contraction phase is relatively rapid, occurring over about 35% of the cycle (and this might be recognized as the systole phase), followed by a relatively long rest or diastole phase which stretches approximately over about 65% of the cycle. For these reasons the mock aorta 40 is designed of elastic or compliant components 60 to more realistically simulate real world, healthy aortic characteristics. That is, as soon as provided an injection of a flow slug approximating seventy-milliliters or so, the elastic 60 of the mock aorta 40 initially expands due to elasticity or compliance, but thereafter each section 60 exerts its own inherent restoring action to return to shape. This compliance property and/or the combination of compliance properties with restoration properties may very likely contribute to motivating the flow 32 onward through the system 28.

Indeed, there may be other factors contributing to motivating the flow 32 along including a ripple or time lag factor. That is, the larger diameter tube sections 60 closest to the mock ventricle 34 likely feel the peak of the pulse earliest, there being a minute lag in the smaller diameter, more distal tube sections 60 feeling the peak of the pulse. In the real world, the response of the human vascular system to the impulses provided by the heart are likely affected by a complex set of factors. The mock aorta structures 40 in accordance with the invention successfully models various ones of these real world factors by means of compliant tube sections 60 having both compliancy and restoration properties, by arranging a series of such tube sections 60 in a progression of diminishing diameter, as well as by provision of suitable axial length (eg., in FIGS. 2 through 4, the vertical distance) for these properties to cooperate in a generally desirable fashion.

Hence the combination of the elastic or compliant tube sections 60 as well as the intermediary flow restrictors 62 allows a user to tune the test apparatus 50 and fairly well achieve various target waveforms in regards of flowrate against time profile and pressure against time profile as well as target forms of the peaks for these profiles as well as target forms for the drop-off too.

The return piping 48 can be reckoned as the rest of the cardiovascular system including the right side of the heart and the lungs. That is, the return piping 48 terminates in a drain into the mock left atrium 30. The mock left atrium 30 comprises a cylindrical plenum having a transparent sidewall of glass or plastic and the like, and sandwiched between stainless steel closures. In use the mock left atrium 30 is only about half full with the circulating fluid 32, the other half comprising simply an air cap. The mock left atrium 30 includes an open air vent 66 in its lid. The return piping 48 is provided with, at approximately its highest elevation, a check valve 68 arranged to permit the suction of air into the return piping 48 during the fall in pressure with the flow pulses. The suctioned-in air is allowed escape through the air vent 66 in the lid of the mock left atrium 30. The circulating-fluid 32's discharge from the mock left atrium 30 is what supplies the mock left ventricle 34 and as the flow 32 passes through a mock left mitral valve (not in view in any drawing, but its embedded position is generally indicated by reference numeral 36).

Another aspect of the mock left atrium 30 includes a heating service. That is, the mock left atrium 30 has heating tubes (not in view in any drawing, preferably stainless steel) looped or coiled inside the lower half of it. These heating tubes carry a thermal fluid (including without limitation distilled water) which is heated by an external heat source (not shown), the heat service being under the control of a control system (not shown). The heat service includes the services of a temperature sensor that will be more particularly referenced below in connection with various other sensors and probes.

Pause can be taken to consider various aspects of the inventive test apparatus 50. One, the test apparatus 50 circulates a working or "circulating" fluid 32 naturally enough, which circulating fluid 32 preferably serves as a blood analog in instances of testing LVAD's. Example blood analogs for the purpose include without limitation compositions of glycerin, distilled water and salts, sometimes fine particles are introduced to simulate the particle characteristics of blood (eg., red blood cells). Also, the circulation loop of the circulating fluid 32 is closed. From an arbitrary origin in the mock atrium 30, all the circulating fluid 32 returns to the mock atrium 30.

Referring briefly to FIG. 1, an LVAD 42 is situated in a bypass loop 70 around the aortic valve 38'. FIGS. 3 and 4 show that hooking up LVAD test samples 42 to the test apparatus 50 comparably involves hooking up such LVAD samples 42 in a bypass loop 70 around the mock aortic valve 38. FIG. 2 on the other hand shows a bath tank 72, which hides from view the test samples 42 in its interior. This bath tank 72 allows submersing the samples 42 during use (ie., testing) in a bath fluid. Suitable bath fluids preferably are a bodily-fluid analog including without limitation distilled water and the like. The bath tank 72 is provided with one or more viewing ports 74 for visual, pictorial or video examination during use.

FIGS. 1, 3 and 4 show that an example LVAD 42 comprises an intake port 76, an exhaust port 78 and one or more communication leads 46. FIG. 1 diagrammatically depicts a mock bypass infeed port 82 in the left ventricle 34 for supplying the intake port 76 of the LVAD. FIGS. 2 and 3 show that one inventive aspect of the test apparatus 50 in accordance with the invention is that it facilitates plural test loops 28—in this case in parallel—for concurrent testing of plural test samples 42 more or less under the same flow conditions. To return for a moment to FIG. 1, the left side of the human heart is indicated generally by reference numeral 28', whereas in FIG. 3 a given test loop 28 is reckoned as the analog to that much of FIG. 1 indicated by reference numeral 28'.

Accordingly, the mock left ventricle 34 is provided with three mock bypass-infeed ports 82 in the mock left ventricle 34 for suppling the test samples 42 with an infeed of a bypass flow of the circulating fluid 32. The exhaust ports 78 of the LVAD's are connected (this connecting piping not shown in the drawings) to discharge hook-ups 84 which empty into the bottom of the mock aortas 40, downstream of the mock aortic valves 38. Hence in actuality the test samples 42 hook-up in the test apparatus 50 in a bypass loop 70 around the mock aortic valves 38' as diagrammatically shown in FIG. 1.

From FIG. 2 it can be discerned that preferably, during use (testing), the customer's test LVAD samples (not in view in this drawing) are submersed in the bath fluid of the bath tank 72. Although no heating service is in view, the bath tank 72 is serviced by a heating service comparable to that described previously in connection with the mock left atrium 30. That is, a thermal fluid is circulated through a heat exchanger comprising loops or coils of stainless steel tube. The control over the heat service is governed by a control system, which is not shown.

Briefly, the control system for the test apparatus 50 can be handled by any suitable device including without limitation a PC or like programmable machine. A PC or like programmable machine is preferable because it can be configures to function concurrently as controller and data recorder, and concurrently for one or more like test apparatus 50 in accordance with the invention. Basic sensors or probes in service for the controller/data-recorder system include without limitation the following. A first pressure tap 86 is arranged to measure ventricle pressure, and this is preferably disposed through the lid of the mock left ventricle 34 as shown in FIG. 2. Plural other pressure taps 88 are arranged to measure the individual pressures of the separate mock aortas 40—which in the drawings are shown to comprise three in number. The pressure taps 88 for the mock aortas 40 are preferably disposed at the base of the tubular columns 60/62 forming the mock aortas 40 or perhaps alternatively in proximity to the LVAD discharge connections 84 into the mock aortas 40.

To consider now the measure of flowrates, each test loop 28 has its own flowmeter 90 on the mock aortas 40 at positions as shown to measure low through that aorta 40 for that test loop 28. Total system flowrate is obtained by summing the flowrates measured by the individual test-loop flowmeters 90. For instance, if all three test loops 28 are in use at once, total flowrate is obtained by summing the flowrates of the individual three test-loop flowmeters 92. In contrast, if only one test loop 28 is in use—as by having the other two test loops 28 shut off by valving or capping and the like—then the total flowrate corresponds to the measure of the one test-loop flowmeter 90 on the only test loop 28 in use. In addition to test-loop flowrate measured with the mock aortas 40, one or more other flowmeters 92 are in service with the test LVAD's, to measure bypass flowrate through each LVAD 42 in service during use. Preferably all the flowmeters 90 and 92 are chosen from ultrasonic varieties which don't require direct insertion into the flow path, but which can remotely sense interior flowrate through ultrasonic probe(s) on the involved piping's exterior.

Also, at least one temperature sensor 94 is arranged on the test apparatus 50. Preferably a single RTD temperature probe 94 is disposed to measure temperature of the bath fluid in the tank 72 therefor, the temperature of the circulating fluid 32 being reckoned from that. All the probes 86, 88, 90 and 92 as well as 94 provide electrical signals for communicating to the controller/data-recorder system(s) for control and data recording purposes. Additionally, the customer's test LVAD samples 42 presumably are the origins of various communications leads 46 which have to be routed out from inside the bath tank 72 to hook-up terminations with power and command module(s) 44 outside the tank 72. Presumptively such LVAD power and command modules 44 are connected in communication with the test apparatus 50's controller/data-recording system.

Given the foregoing, the test apparatus 50 is operable to step through various test modes, including for example a waking rest mode characterized by a pulse rate of seventy beats per minute or so, pulsing about seventy milliliters of circulating fluid 32, producing a mean aortic pressure of 100 mm of mercury or so. The waking rest mode can be switched to different other modes. For example, one other mode might correspond to an exercise mode, characterized by a pulse rate of one-hundred-twenty (120) beats per minute or so, similarly pulsing about seventy milliliters or so of the circulating fluid 32, and producing a mean aortic pressure of about 110 mm of mercury. Additional modes are variously programmable into the control system as desired. For the sake of one further example, a further mode might be sleep mode, characterized by a pulse rate of fifty beats per minute or so, at more or less the same volumetric capacity per pulse as before, perhaps seeing a slight decline in the mean aortic pressure below 100 mm of mercury.

With the above in mind, it is an object of the invention to create a test apparatus 50 providing specific target pulsing or pulsatile flow for qualifying or certifying test samples which operate in such an environment. It is another object of the invention to more specifically re-produce the flow conditions or aspects of the human cardiovascular system. It is an alternate object of the invention that the foregoing is achieved by mock aorta structures constructed in part from elastic or "compliant" tubing components 60. It is a further object of the invention to provide plural test loops 28 in one test apparatus 50 to allow concurrent parallel-processing of test samples 42.

Among the notable achievements are the following. Controlling the switching among the various operative modes—eg., waking rest mode, exercise mode, sleeping rest mode and the like for example—is achieved by the simple expediency of controlling the speed of the servomotor 56. Needless to say the servomotor 56 is connected in communication with the control system. The invention obviates the need for any more complex control over the circulating fluid 32 in order to achieve target waveforms other than control over the servomotor 56.

Put differently, the control system operates on the basis of various inputs taken from the pressure taps 86 and/or 88, the flowrate taps 90 and/or 92 and to a lesser extent the temperature tap(s) 94. Additionally, the control system is likely in communication the test samples 42' power and command modules 44, if any. In consequence, the control system sequences among operative modes merely by sending instruction signals to one component:—that being the servomotor 56. It is important to appreciate that the servomotor 56 alone cannot shape the circulating fluid 32's waveforms as completely as desired. The work that the servomotor 56 cannot provide in shaping the target waveforms is accomplished by the compliant tube components 60 of the mock aortas 40. Prior to an actual testing of samples 42, there is a pre-test procedure involving tuning the test apparatus 50's response to changing flows if provided with and incorporating appropriately built-and-measured compliant tube components 60. After tuning, the compliant tube components 60 can be reliably relied on to shape the waveforms as desired even in response to changing flows. This response property of the compliant tube components 60 is inherent to properly designed, properly built-and measured, and properly tuned components 60. For these reasons, during test operation, the control system only need give control signals to the servomotor 56 to switch among test modes. The work in obtaining the target waveforms which cannot be attained by the servomotor 56 alone is attained by the design, construction and tuning of the compliant components 60 in the columns 60/62.

Whereas the terminology "left" has been used predominantly in connection to referencing one side of the heart in contrast to the other, this is done merely for convenience in the description only and the principles of the invention apply comparably to testing samples in pulsatile or fluctuating flows in general, regardless if these include right-side ventricle assist devices or other things. Needless to say the artery on modeling right-side heart behavior is not referred to as the aorta.

And as mentioned many times previously, whereas the invention has been described predominantly in connection with testing ventricle assist devices, this is done so merely for convenience in the description. The test apparatus 50 can be configured according to the principles of the invention to re-produce or mimic various other kinds of complex pulsing or fluctuating flow environments in the service of a testing samples.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

I claim:

1. A test apparatus providing pulsatile flow service with a blood analog for replicating aspects of the human cardiovascular system in order to certify the operability and/or reliability of a chosen sample device, such as an implantable cardiovascular assist device, with flows and conditions that give the sample device a fairly real trial of operating in the environment of the human cardiovascular system before surgical implantation in a patient; comprising:

a main circulation circuit for the blood analog comprising in series a pump providing flow in a sequence of pulses, a mock left ventricle, a mock aortic valve, a mock aorta, and a return loop that returns to the pump; and a bypass loop to bypass the mock aortic valve, originating on the left ventricle and terminating in the aorta, affording interconnection of the sample device;

wherein the mock aorta comprises a plurality of elastic tube sections connected in series in progression of diminishing diameters, and inter-coupled by an adjustable flow restrictor(s), each elastic tube section selected for a compliance factor measuring between about a 7% to 12% expansion of the inside diameter for a 100 mm mercury step increase of inside pressure; whereby the selection over the compliance factors for the elastic tube sections as well as the adjustability of the intermediary flow restrictor(s) allows a user to tune the test apparatus for shaping various target waveforms in regards of flowrate and pressure against time as well as target forms of the peaks and drop-offs thereof in addition.

2. The test apparatus of claim 1 wherein the pump is driven to provide a mock systole phase occurring over about 35% of one pulse's cycle, followed by a relatively longer rest or mock diastole phase which stretches approximately over about the remaining 65% of the pulse cycle.

3. The test apparatus of claim 1 wherein the pump is driven to provide the sample device with about seventy milliliters of blood analog each pulse as well as is controllable to sequence variously through various modes including:
- a waking rest mode corresponding to a pulse rate of about seventy beats per minute and producing a mean aortic pressure of about 100 mm of mercury;
- an exercise mode corresponding to a pulse rate of about one-hundred twenty beats per minute and producing a mean aortic pressure of about 110 mm of mercury; and
- a sleep mode corresponding to a pulse rate of about fifty beats per minute and producing a mean aortic pressure of about 100 mm of mercury.

4. A test apparatus providing pulsatile flows and replicating the human cardiovascular system for testing devices, comprising:
- a circuit comprising in series a mock left ventricle, a mock aortic valve, a mock aorta, and a pump circulating a fluid returned from the mock aorta in pulsatile flow to the mock left ventricle; and
- a loop from the mock left ventricle to the mock aorta that bypasses the mock aortic valve and affords interconnection of a test device;
- wherein the mock aorta comprises elastic tube sections serially connected from a first-in-progression successively to a last-in-progression, and which are intermediately interconnected by a flow restrictor such that a pulse of fluid inputted to the first-in-progression elastic tube section causes swelling therein that thereupon is discharged through the corresponding flow restrictor into the succeeding elastic tube section, which succeeding elastic tube section correspondingly swells as a result thereof but lagging behind in time; whereby the rippling time lag of swelling in the succeeding elastic tube sections relatively replicates the human cardiovascular system.

5. The test apparatus of claim 4 wherein the mock aorta comprises a plurality of elastic tube sections connected in series in progression of diminishing diameters.

6. The test apparatus of claim 4 wherein each flow restrictor is adjustable.

7. The test apparatus of claim 6 wherein each flow restrictor(s) comprises a valve.

8. The test apparatus of claim 4 wherein each elastic tube section is characterized by about 7% to 12% inside-diameter expansion for 100 mm mercury step increase in pressure.

9. The test apparatus of claim 4 wherein the test device comprises an implantable cardiovascular assist device whereby said test apparatus affords a fairly real trial of operating in the environment of the human cardiovascular system before surgical implantation of such device in a patient.

10. The test apparatus of claim 4 wherein the test device comprises a left ventricle assist device.

11. The test apparatus of claim 4 wherein the pump is driven to provide a mock systole phase occurring over about 35% of one pulse's cycle, followed by a relatively longer rest or mock diastole phase which stretches approximately over about the remaining 65% of the pulse cycle.

12. The test apparatus of claim 4 wherein the pump is driven to provide the test device with about seventy milliliters of fluid each pulse as well as is controllable to sequence variously through various modes including:
- a waking rest mode corresponding to a pulse rate of about seventy beats per minute and producing a mean aortic pressure of about 100 mm of mercury;
- an exercise mode corresponding to a pulse rate of about one-hundred twenty beats per minute and producing a mean aortic pressure of about 110 mm of mercury; and
- a sleep mode corresponding to a pulse rate of about fifty beats per minute and producing a mean aortic pressure of about 100 mm of mercury.

13. A test apparatus providing pulsatile flows and replicating the human cardiovascular system pulsatile flows, comprising:
- a circuit comprising in series a plenum, a check valve, a cardiovascular system, and a pump circulating a fluid returned from the cardiovascular system in pulsatile flow to the plenum;
- wherein the mock cardiovascular system comprises elastic tube sections serially connected from a first-in-progression successively to a last-in-progression, and which are intermediately interconnected by a flow restrictor such that a pulse of fluid inputted to the first-in-progression elastic tube section causes swelling therein that thereupon is discharged through the corresponding flow restrictor into the succeeding elastic tube section, which succeeding elastic tube section correspondingly swells as a result thereof but lagging behind in time; whereby the rippling time lag of swelling in the succeeding elastic tube sections relatively replicates the human cardiovascular system.

14. The test apparatus of claim 13 further comprising a loop from the plenum to the mock cardiovascular system that bypasses the check valve and affords interconnection of a test device.

15. The test apparatus of claim 14 wherein the test device comprises an implantable cardiovascular assist device whereby said test apparatus affords a fairly real trial of operating in the environment of the human cardiovascular system before surgical implantation of such device in a patient.

16. The test apparatus of claim 14 wherein the test device comprises a ventricle assist device.

17. The test apparatus of claim 13 wherein the mock cardiovascular system comprises a plurality of elastic tube sections connected in series in progression of diminishing diameters.

18. The test apparatus of claim 13 wherein each flow restrictor is adjustable.

19. The test apparatus of claim 13 wherein each elastic tube section is characterized by about 7% to 12% inside-diameter expansion for 100 mm mercury step increase in pressure.

20. The test apparatus of claim 13 wherein the pump is driven to provide a mock systole phase occurring over about 35% of one pulse's cycle, followed by a relatively longer rest or mock diastole phase which stretches approximately over about the remaining 65% of the pulse cycle.

21. The test apparatus of claim 13 wherein the pump is driven to provide the test device with about seventy milliliters of fluid each pulse as well as is controllable to sequence variously through various modes including:

a waking rest mode corresponding to a pulse rate of about seventy beats per minute and producing a mean aortic pressure of about 100 mm of mercury;

an exercise mode corresponding to a pulse rate of about one-hundred twenty beats per minute and producing a mean aortic pressure of about 110 mm of mercury; and a sleep mode corresponding to a pulse rate of about fifty beats per minute and producing a mean aortic pressure of about 100 mm of mercury.

* * * * *